United States Patent [19]

Hrebeniuk

[11] Patent Number: Plant 7,755

[45] Date of Patent: Dec. 24, 1991

[54] DISTINCT VARIETY OF POINSETTIA NAMED H-201 WHITE

[76] Inventor: Alexander Hrebeniuk, R.D. #1, Box 118, Sugar Run, Pa. 18846

[21] Appl. No.: 339,527

[22] Filed: Apr. 17, 1989

[51] Int. Cl.[5] ..... A01H 5/00
[52] U.S. Cl. ..... Plt./86
[58] Field of Search ..... Plt./86, 86.2

[56] References Cited

U.S. PATENT DOCUMENTS

P.P. 2,731 4/1967 Mikkelsen ..... Plt. 86

*Primary Examiner*—Howard J. Locker
*Attorney, Agent, or Firm*—Webb, Burden, Ziesenheim & Webb

[57] ABSTRACT

A Poinsettia plant named H-201 White particularly characterized by the combined characteristics of its creamy white bract, compact growth habit with strong branching, dark green leaves, long lasting bloom centers, eight week response time, the plant ships well.

1 Drawing Sheet

BACKGROUND OF THE NEW PLANT

The present invention comprises a new and distinct cultivar of *Euphorbia pulcherrima* known by the varietal name H-201 White. The new cultivar was developed in a breeding program and is a selection resulting from the cross of the male parent H-H 1 White (U.S. Plant Pat. No. 4,219), and the female parent H-524 Creamy White U.S. Plant Pat. No. 6,890. The new cultivar has a longer lasting cyathia, a better stem condition and the growing size is shorter when compared to the parentage.

The new cultivar was discovered in June of 1986 in Sugar Run, Pa.; was first asexually reproduced by cuttings shortly thereafter in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this Poinsettia as new and distinct:

1. Eight week response time under black cloth.
2. Six to eight medium large bracts after pinch.
3. May be grown single stem or pinch. Branching occurs only in response to pinching and plant develops substantial branching after the pinch.
4. Top leaves dark green.
5. Mature leaves lighter in color.
6. Petiole light to medium green.
7. Veins on leaves light green.
8. Stem on top and bottom green.
9. Bracts creamy-white.
10. The center of the bloom is long lasting.
11. Blooms have two layers of bract, dependable growing, type flat.
12. Up to twenty (20) bracts have been counted on a fully developed pinch plant bloom.
13. The largest bloom size measured on a single stem pinch plant has been 13 inches in diameter.
14. Bracts range in size on a pinch plant from three (3) cm. wide by seven (7) cm. long, to eight (8) cm. wide and thirteen (13) long.

15. In normal blooming the new cultivar shows color in October and is fully in bloom the beginning of December.
16. Responds very well to the growth regulator cycocel.
17. Long lasting. Can be raised as a commercial plant for propagation or can be kept as a house plant.
18. Plants ship well. Plants are resistant to bruise and droop.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight week plants. The color readings were determined under natural daylight at Sugar Run, Pa. Color references are primarily to The R.H.S. Colour Chart of The Royal Horticultural Society of London.

The plant:

*Form.*—Double.

*Growth habit.*—Medium height, compact (cyathia are closely united and growing upright), very strong branching with six to eight breaks per pinch. Grows flowers well under cool conditions.

*Rooting.*—Fast and even.

*Blooming season.*—Eight weeks.

*Blooming habit.*—Medium to large bracts develop in double rows. Keeping quality is very good.

*Size.*—The plant height from the soil line is 12 inches to 15 inches and is 15 inches plus or minus up to 3 inches in diameter depending on growing conditions.

Foliage:

*Size.*—From 8 cm. wide and 10 cm. long, to 10 cm. wide and 13 cm. long.

*Quantity.*—Up to eight leaves per stem, long lasting and not falling.

*Color.*—New foliage—Upper side, Green Group 137 A. Under side, Green Group 137 D. Old foliage—Upper side, Green Group 137 C. Under side, Green Group 138 B. Leaf Petiole—Green Group 139 D.

*Shape.*—Bottom leaves heart shaped, top leaves oak shaped.

*Texture.*—Upper side is velvety; under side is smooth between veins.

*Edge of margin.*—Wavy to pointed.

*Disease resistance.*—Good resistance to botrytis.

Flowers:

*Borne.*—In a compound corymb.

*Quantity.*—18 per stem. Number can vary depending on growing conditions with each flower having a nectary.

*Color.*—Organs—Ovaries: Yellow-Green Group 149 B and Yellow-Green Group 149 C. Nectary cups: Yellow-Orange Group 15 A.

Bracts:

*Size.*—From 3 cm. wide to 7 cm. long, to 8 cm. wide and 13 cm. long.

*Shape and Margin.*—Mostly heart shaped with the distal end being from a needle end to hook pointed. Margin: Smooth, wavy. Veins: Midrib to margin.

*Color.*—Yellow Group 4 D.

*Quantity.*—Up to 20 per stem on a pinch plant. The largest bloom size measured on a single stem has been 13 inches in diameter.

Reproductive organs: Typical for Poinsettia cultivars.

When compared to the variety disclosed in U.S. Plant Pat. No. 2,731, H-201White has heart shaped bracts whereas the compared variety has oval shaped bracts. Also, the flower of the new cultivar grows flat and borne is set higher. In addition, the end bracts include a longer point and more bend as compared to the patented variety.

I claim:

1. A new and distinct variety of Poinsettia plant as herein shown and described, particularly characterized by its creamy white bract, compact growth habit with strong branching, dark green leaves, long lasting bloom centers, eight week response time, long blooming, and good shipping characteristics.

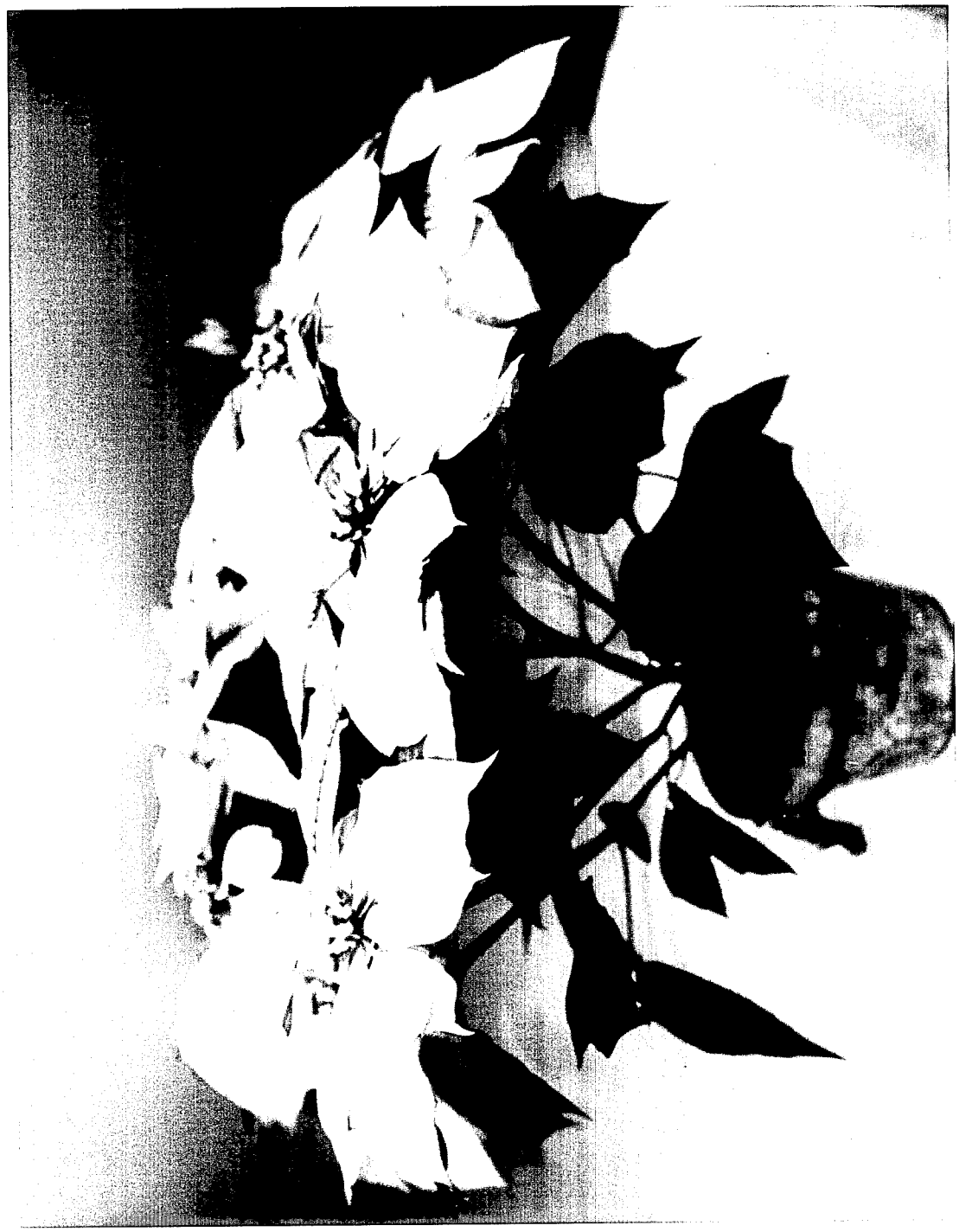

* * * * *